(12) United States Patent
Jang et al.

(10) Patent No.: US 10,080,381 B2
(45) Date of Patent: Sep. 25, 2018

(54) METHOD FOR PREPARING GOCHUJANG AND GOCHUJANG PREPARED BY PREPARATION METHOD

(71) Applicant: CJ Cheiljedang Corporation, Seoul (KR)

(72) Inventors: Eun Seok Jang, Gyeonggi-do (KR); Seon Mi Oh, Gyeonggi-do (KR); Min Kyung Park, Seoul (KR); Hye Won Shin, Seoul (KR); Hyun Jun Jang, Gyeonggi-do (KR); Sung Hwan Lim, Gyeonggi-do (KR); Sun A Cho, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 22 days.

(21) Appl. No.: 15/038,779

(22) PCT Filed: Nov. 28, 2014

(86) PCT No.: PCT/KR2014/011551
§ 371 (c)(1),
(2) Date: May 24, 2016

(87) PCT Pub. No.: WO2015/080514
PCT Pub. Date: Jun. 4, 2015

(65) Prior Publication Data
US 2017/0000171 A1    Jan. 5, 2017

(30) Foreign Application Priority Data

Nov. 29, 2013 (KR) .................. 10-2013-0147561

(51) Int. Cl.
| | |
|---|---|
| A23L 11/20 | (2016.01) |
| A23L 27/50 | (2016.01) |
| A23L 27/24 | (2016.01) |
| A23L 27/12 | (2016.01) |
| C12R 1/69 | (2006.01) |

(52) U.S. Cl.
CPC ............... *A23L 11/20* (2016.08); *A23L 27/12* (2016.08); *A23L 27/24* (2016.08); *A23L 27/50* (2016.08); *C12R 1/69* (2013.01); *A23V 2002/00* (2013.01)

(58) Field of Classification Search
CPC .......... A23L 11/20; A23L 27/50; A23L 27/24; A23L 27/12; C12R 1/69
USPC .......................................................... 426/18
See application file for complete search history.

(56) References Cited

FOREIGN PATENT DOCUMENTS

| | | |
|---|---|---|
| KR | 10-2002-0069788 A | 9/2002 |
| KR | 10-2008-0000427 | 1/2008 |
| KR | 10-2011-0017619 A | 2/2011 |
| KR | 10-1090317 B1 | 12/2011 |
| KR | 10-1280407 B1 | 7/2013 |
| KR | 10-2013-0113608 A | 10/2013 |

OTHER PUBLICATIONS

Park, KR-10-2013-0113608—Machine Translation (Year: 2013).*
Choi et al., Jour. Agri. Sci., 1997, vol. 24, No. 2, p. 283-289, "Physiological Function and Enzyme Activity of Koji Cultured by *Aspergillus oryzae* CNU 04-5 in the Various Grain Materials".
International Search Report dated Mar. 31, 2015 in PCT/KR2014/011551.

* cited by examiner

*Primary Examiner* — Hamid R Badr
(74) *Attorney, Agent, or Firm* — Swanson & Bratschun, L.L.C.

(57) ABSTRACT

The present invention relates to a method for preparing hot pepper paste (gochujang in Korean) by using a novel strain, and hot pepper paste prepared therefrom. More specifically, the hot pepper paste having a consistent quality and improved flavor and taste can be prepared by isolating and selecting *Aspergillus oryzae* having remarkable carbohydrate and protein degradation enzymatic activities from traditional meju (fermented soybeans) by using wheat flour or polished wheat as a substrate, and using the isolated and selected product for preparing the hot pepper paste.

6 Claims, 1 Drawing Sheet
Specification includes a Sequence Listing.

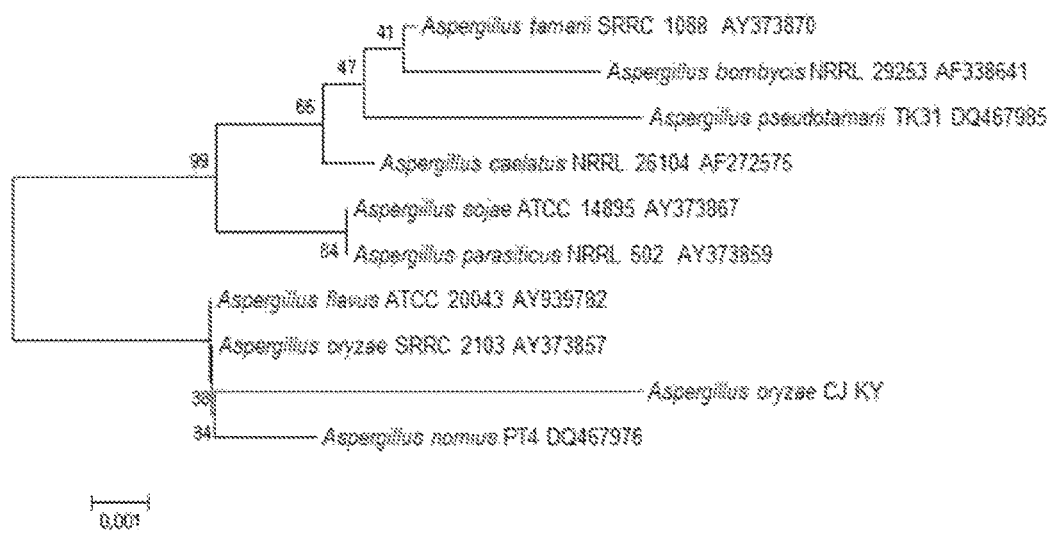

METHOD FOR PREPARING GOCHUJANG AND GOCHUJANG PREPARED BY PREPARATION METHOD

CROSS REFERENCE TO RELATED APPLICATIONS

This application is a National Stage Entry of International Application No. PCT/KR2014/011551 filed on Nov. 28, 2014 (WO 2015/080514), and claims the benefit of Korean Application No. 10-2013-0147561, filed on Nov. 29, 2013, which is hereby incorporated by reference in its entirety for all purposes as if fully set forth herein.

TECHNICAL FIELD

The present invention relates to a method for preparing hot pepper paste (gochujang in Korean) by using a novel strain, *Aspergillus oryzae* isolated from traditional meju (fermented soybeans), and a hot pepper paste prepared therefrom.

More specifically, the present invention relates to a method for preparing hot pepper paste having improved flavor and taste by isolating and selecting a novel strain, *Aspergillus oryzae* CJ KY, *Aspergillus* which has remarkable carbohydrate and protein degradation enzymatic activities from traditional meju using wheat flour or polished wheat as a substrate, and then, by using such strain in the hot pepper paste preparation, and the hot pepper paste prepared therefrom.

Incorporated by reference herein in its entirety is the Sequence Listing entitled "Sequence list.txt", created May 23, 2015, size of 2 kilobytes.

BACKGROUND ART

The kinds of hot pepper paste are largely classified into a conventional hot pepper paste which uses meju for hot pepper paste made by mixing soy and cereal in a constant ratio and an improved type hot pepper paste made by using koji instead of meju for hot pepper paste.

The conventional hot pepper paste is made by a step for mixing the resultant prepared from procedure comprising dipping and cooking starchy raw material and then mixing it with malt extract to proceed a liquid saccharification procedure with meju for hot pepper paste, dried red pepper powder, salt, etc. to fermentat and age it.

The improved type hot pepper paste is made by a step for mixing koji which is obtained by dipping or hydrating and cooking starchy raw material and then cultivating *Aspergillus* in it, with a table salt, cooked starchy raw material, etc.; a step for aging the mixed material; and a step for mixing the aged material with starch sugar, dried red pepper powder, etc. As the starchy material, a wheat flour or polished wheat which has a supply-demand and a unit cost of the raw material and, a processing suitability of the raw material easy for a mass production is mainly used.

As a measure which is available for the mass production, and is for enhancing a quality of hot pepper paste, in the improved type hot pepper paste, Korean Patent Publication No. 10-2011-0017619 suggested a method for preparing koji for rice hot pepper paste with a high enzyme titer, which comprises a step for preparing a koji with a high enzyme titer by cooking a rice raw material limited to from 4-percent to 12-percent polished rice to make 30 to 32 percent by weight of moisture content, and delaying an aging speed of the gelatinized rice to prevent a growth decline of *Aspergillus* by controlling a moisture content and temperature to 35 to 38 percent by weight and 30 to 38° C., respectively through the procedure for containing the moisture, and a step for improving a taste and flavor of the rice hot pepper paste by using the koji.

However, in the case of the prior art as above, although stickiness on a surface of rice can be somewhat reduced, since the lower the polishing level of rice, the contents of a fiber in the rice, there are problems that the degration rate of *Aspergillus* is decreased, and the enzyme titer becomes lower due to the decrease of the growth of *Aspergillus*, and also there is occurred the problem that a mouthfeel of hot pepper paste is decreased.

In order to solve the problems of the prior art as mentioned above, the present inventors developed the method for preparing hot pepper paste with the improved taste and flavor by isolating and selecting a new strain, *Aspergillus oryzae* CJ KY from traditional meju, the strain exhibits high amylase and protease activity with wheat flour or polished wheat, soybean and the like as a substrate, and makes the flavor and taste property such as palatability and sweet flavor (fruit flavor), delicious meju flavor, etc., better, and then, by using such strain in preparing hot pepper paste, and the hot pepper paste prepared by the preparation method, and then have been completed the present invention.

PRIOR ART REFERENCE

Patent Reference (Patent Reference 1) KR 10-2011-0017619

DISCLOSURE

Technical Problem

The object of the present invention is to provide the method for preparing hot pepper paste with the improved flavor and taste by isolating and selecting a new strain, *Aspergillus oryzae* CJ KY from traditional meju, the strain exhibits high enzyme titer with wheat flour and polished wheat as a substrate and then, by using such strain in preparing hot pepper paste, and the hot pepper paste prepared by such preparation method.

Technical Solution

To achieve the above-mentioned object, the present invention relates to a method for preparing hot pepper paste by using *Aspergillus oryzae* CJ KY, which comprises:

a cooking step for hydrating wheat flour raw material and cooking it;

a jaekuk step (a fermentation step) for preparing wheat flour koji by inoculating and cultivating *Aspergillus oryzae* CJ KY (KCCM11302P) on the cooked wheat flour;

a first aging step for adding a table salt or salt water to the wheat flour koji and aging the first mixture made by mixing the wheat flour koji with at least one selected from the group consisting of cooked wheat flour, cooked polished rice, cooked soybean, meju and doenjang; and a second aging step for adding the dried red pepper flour to the first aged mixture, and for sterilizing and aging the second mixture made by mixing the first mixture obtained from the first aging step with at least one selected from the group consisting of starch sugar, soy sauce, salt, processed goods of spice, taste and flavor enhancer, cereal product, soy product, meju and doenjang.

In addition, the present invention provides the hot pepper paste made by the above method for preparing hot pepper paste.

Advantageous Effects

The present invention has an effect that can prepare hot pepper paste having a consistent quality and improved flavor and taste by isolating and selecting a new strain, *Aspergillus oryzae* CJ KY exhibiting the enzymatic titer with wheat flour or polished wheat as a substrate from traditional meju, and then, by using such strain in preparing the hot pepper paste.

DESCRIPTION OF DRAWINGS

FIG. 1 represents a classification distribution diagram of new strain, *Aspergillus oryzae* CJ KY.

BEST MODE FOR INVENTION

The present invention relates to a new strain, *Aspergillus oryzae* CJ KY, which exhibits the improved carbohydrate and proteolytic enzyme activity with wheat flour and polished wheat as a substrate, and is isolated and selected from traditional meju.

The *Aspergillus oryzae* CJ KY was isolated and selected from traditional meju collected from the traditional food manufacturer.

Isolation•selection method firstly selected six (6) kinds of *Aspergillus oryzae* strains which can be utilized as the *Aspergillus* strain, since they have good spore productivity, do not generate toxin and do not cause allergy in molds isolated from the traditional meju. And then, the first selected strains were cultivated in a solid state by using the wheat flour as the raw material to select the second strains which have a strong power in decomposing carbohydrate and protein, and then strains improving the taste and flavor of hot pepper paste among the selected second strains was finally selected. The finally selected strain was named as *Aspergillus oryzae* CJ KY, and deposited to the Korean Culture Center of Microorganisms (KCCM) (the Deposit No. KCCM 11302P) on Sep. 27, 2012.

In addition, the present invention relates to a method for preparing hot pepper paste by fermenting the cooked wheat flour with *Aspergillus oryzae* CJ KY, which is a strain having strong carbohydrate- and protein-degradation ability and also enhancing flavor and taste of the hot pepper paste with the wheat flour as a substrate.

More specifically, the present invention provides the method for preparing hot pepper paste, which comprises:

a cooking step for hydrating wheat flour raw material and cooking it;

a jaekuk step (a fermentation step) for preparing wheat flour koji by inoculating and cultivating *Aspergillus oryzae* CJ KY on the cooked wheat flour;

the first aging step for adding table salt or salt water to the wheat flour koji and aging the first mixture made by mixing the wheat flour koji with at least one selected from the group consisting of cooked wheat flour, cooked polished rice, cooked soybean, meju and doenjang;

the second aging step for adding the dried red pepper flour to the first aged mixture, and then for sterilizing and aging the second mixture made by mixing the mixture with at least one selected from the group consisting of starch sugar, soy sauce, salt, spice of processed goods, taste and flavor enhancer, cereal product, soy product, meju and doenjang.

In the method for preparing hot pepper paste, the above cooking step is the procedure hydrating the wheat flour with the constant amounts of the warmed purified water by using a continuous pressure cooker and then cooking it by using 1.0 to 2.0 kgf/cm$^2$ of steam, and wherein it is preferable to control the water content of the cooked wheat flour to be 30 to 38 wt %.

In the method for preparing hot pepper paste of the present invention, the above jaekuk step (a fermentation step) is the step for making wheat koji by inoculating and cultivating *Aspergillus oryzae* on the above cooked wheat flour, and specifically the wheat koji is made by mixing the cooked wheat flour with 0.1 to 0.3 wt % of *Aspergillus oryzae* CJ KY and 0.5 to 1.5 wt % of wheat flour or soy flour as an extender, based on the total of weight of raw materials, and then by fermenting at 30 to 40° C., more preferably 33 to 38° C. for 3 days and drying it.

In the method for preparing hot pepper paste of the present invention, the first aging step mentioned above is the step adding table salt or salt water to the wheat flour koji and aging the first mixture made by mixing the wheat flour koji with at least one selected from the group consisting of cooked wheat flour, cooked polished rice, cooked soybean, meju and doenjang.

Specifically, table salt or salt water is added to the wheat flour koji in the dried state through the cooking step, and the first mixture, which is made by mixing the wheat flour koji with at least one selected from the group consisting of cooked wheat flour, cooked polished rice, cooked soybean, meju and doenjang, is aged by fermenting it at 25 to 35° C. for 5 to 30 days.

The above table salt or salt water can be preferably added to be a content of 5 to 10 wt % to the first mixture.

The above soy product means one produced by using soy as a main raw material, and meju or doenjang is not specifically limited and anything already known can be used.

At least one selected from soy product, meju and doenjang can be preferably added to be 0.1~15 wt % of the total weight of the first mixture.

Meanwhile, in order to enhance the taste and flavor of hot pepper paste, selectively, yeast culture medium can be additionally added to the first mixture. The above available yeast is not specifically limited, and for example, strains of *Saccharomyces* sp. *Zygosaccharomyces* sp. or *Pichia* sp. can be used.

The first mixture mentioned above can include water content to be 40 wt % to 55wt %, based on the total weight of the first mixture.

In addition, the first mixture mentioned above can comprise the Chopping process before the aging step.

The above Chopping step means a process cutting the first mixture into a small sized material, and the size is not specifically limited, but it can be chopped in a size of preferably greater than 0 to 20 mm (based on the size of an internal diameter of an amorphous particle of the first mixture), more preferably 1 to 10mm, the most preferably 1 to 5 mm.

When the Chopping process is proceeded before aging the first mixture mentioned above, since it is easy for the enzyme to penetrate into a deep part of the cereal, there are advantages that more various taste and flavor can be generated, and the aging time can be shorten, as well as a sensual factor such as mouthfeel of hot pepper paste, and so on is improved.

The first mixture mentioned above is preferably fermented and aged at 25 to 35° C. for 5 to 30 days.

In the method for preparing hot pepper paste of the present invention, the second aging step mentioned above refers to the step adding the dried red pepper flour to the first aged mixture, and then sterilizing and aging the second mixture made by mixing the mixture with at least one selected from the group consisting of starch sugar, soy sauce, salt, processed goods of spices, taste and flavor enhancer, cereal product, soy product, meju and doenjang.

Specifically, the dried red pepper flour is added to the first aged mixture mentioned above, and then, the second mixture made by mixing the mixture with at least one selected from the group consisting of starch sugar, soy sauce, salt, processed goods of spices, taste and flavor enhancer, cereal product, soy product, meju and doenjang is sterilized at 55 to 85° C. for 1 to 60 minutes, and then is aged by adding the edible alcohol.

The dried red pepper flour can be added to be 6 to 25 wt % of the total weight of the second mixture, and at least one selected from the group consisting of starch sugar, soy sauce, salt, processed goods of spices, taste and flavor enhancer, and cereal product is preferably added to be 15 to 40 wt % of the total weight of the second mixture.

The dried red pepper flour, starch sugar, soy sauce, salt, processed goods of spices, taste and flavor enhancer and cereal product, soy product, meju and doenjang are not specifically limited, and anything already known can be used.

Non-limiting example of the processed goods of spices mentioned above can include the dried seasoned red pepper sauce or the wet seasoned red pepper sauce, and the like.

Non-limiting example of the above taste and flavor enhancer includes yeast extract, soy or wheat protein extract, and the like.

Non-limiting example of the above meju and doenjang can include the improved soybean lumps, Hansik meju, etc. and the improved doenjang, Hansik doenjang, etc.

Hereinafter, the content of the present invention will be illustrated in detail by Examples. But, these Examples are merely provided so that one can understand the content of the present invention, and the scope of the present invention is not limited by these Examples.

EXAMPLE

Example 1

Isolation•Identification and Selection of Microorganisms Derived from the Traditional Meju 1) Isolation•Identification of Microorganisms The strain used as a starter in the present invention was isolated and selected from the traditional meju obtained from traditional foods manufacturers located in Gyeonggi, Gangweon, Chungbuk, and Jeonnam.

As a medium for isolating mold, potato dextrose agar (Difco) medium to which 20 μg/ml of chloramphenicol was added was used, thirty-two (32) molds inhabited as dominance species were isolated and identified, and the identification results are represented in Table 1.

2) The First Selection

After totally considering ones which can be used as Koji mold, such as ability generating spores of thirty-two (32) kinds of molds isolated from the above traditional meju, etc., six (6) kinds of molds were selected as the first one.

The first selected strains were CJ 1334, CJ 1335, CJ 1336, CJ 1354, CJ KY, CJ KG, and the results for the ability for generating spores of them are as follows.

TABLE 1

Results for identifying strains isolated from the traditional meju and the ability for generating spore of each strain

| Strain No. | Identification result | Ability for generating spore | Note. |
|---|---|---|---|
| CJ 1333 | Aspergillus oryzae | ** | |
| CJ 1334 | Aspergillus oryzae | *** | |
| CJ 1335 | Aspergillus oryzae | *** | |
| CJ 1336 | Aspergillus oryzae | *** | |
| CJ 1337 | Aspergillus flavus | * | Generating a toxin |
| CJ 1338 | Aspergillus niger | *** | |
| CJ 1339 | Aspergillus flavus | * | Generating a toxin |
| CJ 1340 | Aspergillus tubingensis | *** | Black koji fungus |
| CJ 1341 | — | x | Ungenerating spores |
| CJ 1342 | Aspergillus sydowii | ** | |
| CJ 1343 | Penicillum polonicum | * | |
| CJ 1344 | Mucor racemosus | ** | |
| CJ 1345 | Penicillium polonicum | * | Causing allergy |
| CJ 1346 | Mucor racemosus | *** | |
| CJ 1347 | Penicillium polonicum | * | |
| CJ 1348 | Emericella nidulans | * | Causing allergy |
| CJ 1349 | Talaromyces spectabilis | ** | |
| CJ 1350 | Emericella rugulosa | ** | Causing allergy |
| CJ 1351 | Mucor racemosus | *** | |
| CJ 1352 | Emericella dentata | * | Causing allergy |
| CJ 1353 | Mycocladus corymbiferus | *** | |
| CJ 1354 | Aspergillus oryzae | *** | |
| CJ 1355 | Mycodladus corymbiferus | *** | |
| CJ 1356 | Aspergillus flavus | *** | Generating a toxin |
| CJ 1357 | Absidia corymbifera | * | |
| CJ 1358 | Aspergillus oryzae | ** | |
| CJ 1359 | Aspergillus oryzae | ** | |
| CJ 1360 | Aspergillus vadensis | ** | |
| CJ 1361 | — | * | |
| CJ 1362 | — | * | |
| CJ KY | Aspergillus oryzae | *** | |
| CJ KG | Aspergillus oryzae | *** | |

3) The Second Selection

Wheat koji for six species of the first selected strains was prepared and then the superior strains were secondly selected by comparing amylase and protease enzyme titers to each other.

The above wheat flour koji was hydrated to be 33 to 38 wt % of water content of 1 kg of the wheat flour with a five stage continuous pressure cooker, and then cooked at 120° C. for 15 minutes by using an Autoclave, and was cooled to 35° C. after cooking. 0.2 wt % of the firstly selected strain was mixed to the cooked wheat flour as cooled, based on the total weight of raw materials and then was cultivated at 35° C. for 3 days, respectively, and the enzyme titer for each wheat flour koji is the same as Table 2.

From the results of the below Table 2, 4 species of strains, CJ 1334, CJ 1354, CJ KY, CJ KG strains which exhibit excellent amylase and protease enzyme titers were secondly selected.

TABLE 2

Comparison of the enzyme titer of the wheat flour
koji applied with firstly selected strains

|  | Amylase titer (U/g) | Protease titer (U/g) |
|---|---|---|
| CJ 1333 | 439.4 | 118.4 |
| CJ 1334 | 565.9 | 140.4 |
| CJ 1335 | 496.6 | 131.6 |
| CJ 1336 | 536.7 | 109.1 |
| CJ 1354 | 542.4 | 105.3 |
| CJ KY | 537.6 | 146.1 |
| CJ KG | 553.3 | 134.0 |

In the above Table 2, the determination process of amylase enzyme titer used the coenzyme which was diluted by 100 folds, being obtained by extracting wheat flour koji in aqueous 2% NaCl solution at 30° C. for 1 hour and filtering it. The enzyme reaction liquid was prepared by adding 1 ml of the crude enzyme liquid, 2 ml of 1% starch sugar as the substrate, 2 ml of phosphate buffer, pH 5.2, and it was reacted at 40° C. for 30 minutes and then the reaction was stopped by adding 10 ml of 0.1N $CH_3COOH$. After reacting it at 40° C. for 30 minutes, 10 ml of 0.1N $CH_3COOH$ was added to stop the reaction. To the enzyme reaction solution after completing the reaction was added 10 ml of 0.005% $KI+ I_2$ solution and it was developed to determine an absorbance at 660 nm by using UV spectrophotometer.

In addition, the determination process of protease enzyme titer used wheat flour koji as coenzyme liquid after extracting it from the distilled water at 30° C. for 1 hour and filtering it. The enzyme reaction liquid was reacted at 38° C. for 1 hr by adding 0.5 ml of coenzyme liquid, 1.5 ml of 2% McIlivine buffer (pH 6.0). And then, the reaction was stopped by adding 3 ml of 0.4M TCA solution and after filtering it, 5 ml of 0.4M $Na_2CO_3$ and 1 ml of phenol reagent were added and sufficiently mixed, and then developed at 38° C. for 30 minutes, and the absorbance at 660 nm was determined by using the spectrophotometer. At this time, the enzyme activity was defined the amounts of enzyme generating tyrosine corresponding to 1 μg for 1 minute as 1 unit and calibration curve was prepared by using tyrosine as a standard material.

4) The Final Selection

The volume of wheat flour koji was enlarged and prepared for four species of the above strains secondly selected and the amylase and protease enzyme titers were compared to each other, and then the taste quality of doenjang prepared by using it was compared and the excellent strains were finally selected.

The above wheat koji was cooked for 10 kg of wheat flour to be 33 to 38 wt % of water contents with the five-stage continuous pressure cooker, and cooled to 35° C. after cooking. The secondly selected strains in amounts of 0.2 wt % relative to the total weight of the raw material were mixed with the cooked wheat flour and then were cultivated at 30 to 35° C. for days with a solid fermenter, respectively, and enzyme titers for each wheat flour koji are the same as the below Table 3.

In addition, the first mixture was prepared by mixing the above wheat flour koji with a table salt or salt water, cooked wheat flour, cooked polishing rice, cooked soybean, meju or doenjang, and then was aged at 25 to 35° C. for 5 to 30 days. The dried red pepper flour was added to the first aged mixture, the mixture was mixed with at least one selected from the group consisting of starch sugar, soy sauce, salt, processed goods of spices, taste and flavor enhancer, cereal product, soy product, meju and doenjang to obtain the second mixture, the second mixture was sterilized and secondly aged to prepare hot pepper paste, and then the simplified sensory test for the hot pepper paste was performed, and the test results are the same as the below Table 3.

From the results of Table 3, CJ KY strain which exhibits the best amylase and protease enzyme titers and the best taste quality was finally selected.

Classification dendrogram of CJ KY, the finally selected strain is illustrated in FIG. 1. In addition, a base sequence analysis result for 16S rDNA of the finally selected strain CJ KY is represented in SEQ ID. No. 1.

TABLE 3

Comparison of enzyme titer for wheat flour koji
to which the secondly selected strain was applied
and the taste quality of hot pepper paste

|  | Amylase titer (U/g) | Protease titer (U/g) | Simplified sensory evaluation |
|---|---|---|---|
| CJ 1334 | 393.6 | 104.2 | 3.39 |
| CJ 1354 | 440.1 | 140.5 | 3.72 |
| CJ KY | 546.8 | 157.4 | 3.95 |
| CJ KG | 477.3 | 163.3 | 3.67 |

Example 2

Preparation of Hot Pepper Paste

1) Cooking and Jekuk Steps

Wheat flour kojies comprising *Aspergillus oryzae* CJ KY, the above finally selected strain and the commercial *Aspergillus oryzae*, respectively were prepared as Example 1 and Comparative Example and then the enzyme titers were compared.

Experimental Example 1

The Preparation of Wheat Flour Koji to which New
*Aspergillus oryzae* CJ KY was Applied After cooking 12,000 kg of wheat flour to be 30 to 38 wt % of water content with 5 stage continuous extender, it was cooled at the temperature of 35 to 40° C. by using a cool air emitter and then transferred into a jekuk room. Then, new *Aspergillus oryzae* CJ KY was inoculated in 0.1 wt % of the weight of wheat flour and a jekuk fermentation procedure was performed at 33 to 38° C. for 3 days.

The enzyme titer of wheat flour koji to which new *Aspergillus oryzae* CJ KY was applied is the same as the below Table 4.

Comparative Example 1

The Preparation of Wheat Flour Koji to which the
Customary *Aspergillus oryzae* was Applied After cooking 12,000 kg of wheat flour to be 30 to 38 wt % of water content with 5 stage continuous extender, it was cooled at the temperature of 35 to 40° C. and then transferred into the jekuk room. Then a conventional *Aspergillus oryzae* was inoculated in 0.1 wt % of the weight of wheat flour and the jekuk fermentation procedure was performed at 33 to 38° C. for 3 days.

The enzyme titer of wheat flour koji to which the conventional *Aspergillus oryzae* was applied is the same as Table 4.

TABLE 4

The enzyme titer of wheat flour koji to which new *Aspergillus oryzae* CJ KY and the conventional *Aspergillus oryzae* were applied

|  | Amylase Titer (U/g) | Protease Titer (U/g) |
|---|---|---|
| Experimental Example 1 | 498 | 142 |
| Comparative Example 1 | 467 | 108 |

From the results of the above Table 4, it could be identified that Amylase and Protease enzyme titers of wheat flour koji to which new *Aspergillus oryzae* CJ KY was applied was increased 6.2% and 29.1% than those of wheat flour koji to which the conventional *Aspergillus oryzae* are applied, respectively.

2) The First Aging Step

After preparing the first mixture by using wheat flour koji of the above Experimental Example 1 and Comparative Example 1 as the below Experimental Example 2 and Comparative Example 2, it was aged at 25 to 35° C. for 5 to 30 days.

Experimental Example 2

The Preparation of the First Mixture by Using New *Aspergillus oryzae* CJ KY

The wheat flour koji prepared by Experimental Example 1 was mixed with 5 to 15 wt % of the cooked polishing rice and 0.1 to 15 wt % of at least one selected from the group consisting of the cooked wheat flour, the cooked soybean, meju and doenjang, based on the total weight of the first mixture and mixed with salt water or table salt to prepare the first mixture in which the final water content and salinity of the first mixture was 45 wt % and 7.5 wt %, respectively.

The first mixture prepared by mixing at least one selected from the group consisting of the cooked wheat flour, the cooked soybean, meju and doenjang was aged.

The general ingredients of the first mixture to which new *Aspergillus oryzae* CJ KY was applied are the same as Table 5.

The volatile scent ingredients of the first mixture to which new *Aspergillus oryzae* CJ KY was applied are the same as Table 6.

Comparative Example 2

Preparation of the First Mixture by Using the Conventional *Aspergillus oryzae*

The wheat koji prepared by the Comparative Example 1 was mixed with 5 to 15 wt % of the cooked polished rice, 0.1 to 15 wt % of one selected from the group consisting of the cooked wheat flour, the cooked soybean, meju and doenjang, and was mixed with salt water or table salt to prepare the first mixture wherein the final water content and salt salinity were 45 wt % and 7.5 wt %, respectively.

The fist mixture mixed with at least one selected from the group consisting of the cooked wheat flour, the cooked soybean, meju and doenjang was aged.

The general ingredients of the first mixture to which the conventional *Aspergillus oryzae* was applied are the same as Table 5.

The volatile flavor ingredients of the first mixture to which the conventional *Aspergillus oryzae* was applied are the same as Table 6.

TABLE 5

Comparison of the general ingredients in the first mixture

|  | Water content (%) | Salinity (%) | Level of aging (mg %) | Reduction sugar (%) | pH |
|---|---|---|---|---|---|
| Experimental Example 2 | 53.4 | 7.02 | 401 | 25.1 | 4.64 |
| Comparison Example 2 | 53.9 | 7.42 | 360 | 22.8 | 4.72 |

From results of the above Table 5, it could be identified that the level of aging and the reduction sugar of the first mixture to which new *Aspergillus oryzae* was applied were increased to 11.4% and 10.1%, respectively.

TABLE 6

Comparison of the main volatile flavor ingredients of the first mixture and hot pepper paste (unit: peak area %)

| The main volatile flavor ingredients | The first mixture | | | hot pepper paste | | |
|---|---|---|---|---|---|---|
|  | Comparative Example 2 | Experimental Example 2 | p value | Comparative Example 2 | Experimental Example 2 | p value |
| 2-methyl butanal | 0.09 ± 0.00 | 1.12 ± 0.10 | 0.005 | 0.14 ± 0.01 | 0.33 ± 0.03 | 0.016 |
| 3-methyl butanal | 0.21 ± 0.01 | 0.68 ± 0.01 | 0.001 | 0.19 ± 0.01 | 0.58 ± 0.03 | 0.003 |
| 2-methoxy phenol | 0.05 ± 0.00 | 0.09 ± 0.00 | 0.020 | 0.07 ± 0.00 | 0.09 ± 0.01 | 0.155 |
| butanedioic acid, diethyl ester | 0.19 ± 0.02 | 0.56 ± 0.01 | 0.002 | 0.2 ± 0.01 | 0.35 ± 0.03 | 0.033 |
| butanoic acid, 3-methylbutyl ester | 0.20 ± 0.01 | 0.37 ± 0.02 | 0.015 | 0.14 ± 0.01 | 0.16 ± 0.02 | 0.349 |
| phenol | 0.42 ± 0.01 | 0.03 ± 0.00 | 0.000 | 0.22 ± 0.03 | 0.02 ± 0.00 | 0.006 |
| 1-hexanol | 0.51 ± 0.04 | 0.23 ± 0.03 | 0.012 | 0.19 ± 0.03 | 0.10 ± 0.03 | 0.117 |
| 1,3-butanediol | 0.78 ± 0.03 | 0.27 ± 0.01 | 0.003 | 0.49 ± 0.01 | 0.27 ± 0.06 | 0.031 |

TABLE 6-continued

Comparison of the main volatile flavor ingredients of the first mixture and hot pepper paste (unit: peak area %)

| The main volatile flavor ingredients | The first mixture | | | hot pepper paste | | |
|---|---|---|---|---|---|---|
| | Comparative Example 2 | Experimental Example 2 | p value | Comparative Example 2 | Experimental Example 2 | p value |
| 1-butanol, 3-methyl | 1.24 ± 0.08 | 0.35 ± 0.02 | 0.004 | 0.98 ± 0.00 | 0.94 ± 0.03 | 0.184 |

From the results of the above Table 6, it could be identified that Experimental Example 2 had the higher ratio of 2/3-methyl butanal which exhibits delicate flavor and scent of fungi of meju, and Butanedioic acid, diethyl ester, butanoic acid, 3-methylbuthyl ester which generates fruit flavor to attribute the overall taste and flavor relatively than that of the Comparative Example 2.

In addition, since Comparative Example 2 had green, floral flavor of the total flavor ingredients, it was shown that it had the higher content of 1-hexanol which can be off-flavor as unripe flavor, greenish taste and phenol which generates acrid flavor than the Experimental Example 2. And, since Experimental Example 2 had the contents of 1,3-butanediol, 1-butanol, 3-methy which can be represented as damp flavor in hot pepper paste such as creamy, cheese flavor and the like lower than the Comparative Example 2, it was considered that hot pepper paste of Experimental Example 2 had less taste and flavor which negatively attributes to the consumers.

3) The Second Aging Step

The second mixture was prepared by using the first mixtures of Experimental Example 2 and Comparative Example 2 which experienced the above first aging step, as the below Experimental Example 3 and Comparative Example 3, and then the second mixtures of Experimental Example 3 and Comparative Example 3 were sterilized and aged to prepare hot pepper paste. In addition, the flavor contents of each hot pepper paste prepared were compared to each other.

Experimental Example 3

Preparation of the Second Mixture to which New *Aspergillus oryzae* CJ KY is Applied 1 to 25 wt % of the commercial dried red pepper flour, 10 to 25 wt % of the wet seasoned red pepper sauce, 15 to 30 wt % of starch sugar, 0 to 0.3 wt % of the taste and flavor enhancer (soybean protein extract), 0 to 1 wt % of soy sauce and 0 to 1 wt % of salt, based on the total weight of the second mixture were put into the first mixture which completed the fermentation and aging steps for 5 to 30 days according to the above Experimental Example 2, and mixed it. Then, it was sterilized at 65° C. for 15 to 20 minutes, cooled, and then 1 to 2 wt % of the edible alcohol was added and aged.

The free amino acids of doenjang prepared by sterilizing and aging the second mixture to which new *Aspergillus oryzae* CJ KY was applied are the same as Table 7.

Comparison Example 3

Preparation of the Second Mixture to which the Conventional *Aspergillus oryzae* was Applied 1 to 25 wt % of the commercial dried red pepper flour, 10 to 25 wt % of the wet seasoned red pepper sauce, 15 to 30 wt % of starch sugar, 0 to 0.3 wt % of the taste and flavor enhancer (soybean protein extract), 0 to 1 wt % of soy sauce and 0 to 1 wt % of salt, based on the total weight of the second mixture were put into the first mixture which completed the fermentation and aging steps for 5 to 30 days according to the above Comparative Example 2, and mixed it. Then, it was sterilized at 65° C. for 15 to 20 minutes, cooled, and then 1 to 2 wt % of the edible alcohol was added and aged.

The free amino acids of hot pepper paste prepared by sterilizing and aging the second mixture to which conventional *Aspergillus oryzae* was applied are the same as Table 7.

TABLE 7

Analysis of the contents for the total amino acids and the main organic acids of the second mixture (g/kg)

| Items | Comparative Example 3 | Experimental Example 3 | p value |
|---|---|---|---|
| The total amino acids | 23.05 ± 0.11 | 26.68 ± 0.10 | 0.028 |
| The total organic acids | 6.72 ± 0.09 | 6.45 ± 0.06 | 0.033 |
| Acetic acid | 0.55 ± 0.08 | 0.64 ± 0.06 | 0.015 |
| Lactic acid | 1.48 ± 0.07 | 0.83 ± 0.05 | 0.011 |
| Succinic acid | 0.33 ± 0.02 | 0.36 ± 0.03 | 0.986 |

It could be identified that Experimental Example 3 had significantly high contents of the total amino acids as the results of the above Table. It was increased to about 31% than the protease activity of the strain of the Comparative Examples (Table 4), it could be identified that the decomposition of the protein was activated, and it could be expected that amino acid-based taste properties (palatable taste, sweet taste, etc.) were exhibited relatively stronger than Comparative Examples.

In addition, there was no great difference in succinic acid of the representative acetic acid, lactic acid and succinic acid as generated during the fermentation procedure in organic acids which affect the taste, but there was a significant difference in acetic acids and lactic acids. Since lactic acid exhibits the tarty sour taste than the fresh sour taste of acetic acid, Experimental Example had the higher ratio of acetic acid and the lower ratio of lactic acid relatively than Comparative Example, and thus it can be considered to positively influence the taste rough and aftertaste preference (Table 8).

Example 3

Estimation of Hot Pepper Paste

Sensory evaluation of hot pepper paste was performed on 200 of 30 to 49 years old women lived in Seoul and Kyeonggi-do by using the improved type hot pepper paste with the traditional starchiness prepared by the above Comparative Example 3 and Experimental Example 3, and hot pepper paste prepared with new *Aspergillus oryzae* CJ KY.

The sensory evaluation was performed in the manner testing the preference on the detailed taste properties based on a scale of 0 to 5. The results of the above sensory evaluation are the same as the below Table 8.

In addition, a profile analysis was performed on 10 trained panels, and an average value was provided by repeatedly estimating it 3 times. The results of the above profile analysis are the same as the below Table 9.

TABLE 8

Sensory evaluation of hot pepper paste (Preference, Scale of 5 points)

| Taste property | Comparative Example 3 | Experimental Example 3 |
|---|---|---|
| Overall taste | 3.94 | 4.12 |
| Color | 4.07 | 4.12 |
| Flavor | 3.62 | 3.79 |
| Mouth touch | 3.71 | 3.88 |
| Aftertaste | 3.76 | 3.91 |
| Hot taste | 4.00 | 4.00 |
| Salty taste | 3.35 | 3.38 |
| Sweet taste | 3.48 | 3.77 |
| Palatable taste | 3.5 | 3.68 |
| Thickness | 4.12 | 3.92 |
| Level of harmony in stir-fried foods | 3.77 | 3.96 |
| Level of harmony in spicy/flour based foods | 4.00 | 4.12 |
| Level of harmony in stew/soup cooking | 3.31 | 3.38 |

TABLE 9

Profile analysis of hot pepper paste (Flavor, taste/taste and flavor, Scale of 15 points)

| | Property | Existed | Changed | p-value |
|---|---|---|---|---|
| Flavor | Sweet flavor | 4.90 | 5.57 | 0.083 |
| | Salty flavor | 5.33 | 5.93 | 0.095 |
| | Bitter flavor | 2.60 | 2.03 | 0.005 |
| | Sour flavor | 1.53 | 1.50 | 0.860 |
| | Spicy flavor | 6.30 | 6.00 | 0.448 |
| | Acrid flavor of the dried red pepper flour | 2.77 | 3.23 | 0.158 |
| | Meju flavor | 5.03 | 4.47 | 0.315 |
| | Soy source flavor | 4.07 | 5.00 | 0.010 |
| Taste | Sweet taste | 5.63 | 7.20 | 0.000 |
| | Salty taste | 8.00 | 9.43 | 0.000 |
| | Bitter taste | 3.20 | 2.10 | 0.000 |
| | Sour taste | 1.73 | 1.47 | 0.109 |
| | Umami | 6.40 | 7.90 | 0.000 |
| Taste and flavor | Flavor of the red pepper | 3.87 | 2.23 | 0.000 |
| | Acrid flavor of the dried red pepper flour | 4.27 | 2.20 | 0.000 |
| | Taste and flavor of meju flour | 2.90 | 4.80 | 0.000 |
| | Savory taste and flavor of barley | 2.13 | 3.97 | 0.000 |
| | Flavor of soy sauce | 4.77 | 6.37 | 0.000 |
| | Starch syrup | 3.97 | 5.80 | 0.000 |
| | metallic | 1.40 | 2.87 | 0.000 |
| Mouth feeling | Hot | 10.07 | 9.43 | 0.010 |
| | Sharp | 6.73 | 5.93 | 0.002 |
| | Astringent/Convergent | 5.77 | 5.00 | 0.011 |
| | Soupy | 7.13 | 6.33 | 0.001 |
| | Fine degree of particles | 6.27 | 7.17 | 0.001 |
| | powdery feeling | 5.87 | 4.90 | 0.003 |
| | Thickness | 6.10 | 7.17 | 0.002 |
| | Durability | 7.13 | 8.03 | 0.004 |
| Appearance | Degree of red | 8.00 | 8.80 | 0.004 |
| | Degree of black | 6.63 | 6.20 | 0.357 |
| | Glossy | 7.67 | 6.67 | 0.000 |
| | Thickness | 6.77 | 7.87 | 0.002 |

From the results of the above Tables 8 and 9, Experimental Example 3 exhibited significant lower level than Comparative Example 3 in bitter flavor, bitter taste, soupy, etc., and it exhibited significant higher level than Comparative Example 3 in starch syrup flavor, umami, taste and flavor of meju flour, etc. Experimental Example 3 was evaluated as being high in palatable taste, after taste, sweet taste, mouth feeling, etc. and it was evaluated as being high than Comparative Example 3 in the overall taste. It is considered that the decomposition rate of starch and protein contained in wheat flour and the polished rice became high due to high enzyme titer of new *Aspergillus oryzae* CJ KY, and thus, by the reduction of the undecomposed starch, the positive effect on the preference of sweet taste and soupy (powdery feeling), and the fermentation products such as the free amino acids, etc. generated as large amounts were appeared as palatable taste and meju flour taste and flavor, etc., and thus the positive effect influence on the improvement of the taste quality of hot pepper paste.

[Deposit Number]
Name of Depository: Korean Culture Center of Microorganisms (KCCM) (Foreign country)
Deposit No.: KCCM11302P
Deposit Date: Sep. 27, 2012

The invention claimed is:

1. A method for producing hot pepper paste, which comprises:
   a heating step for hydrating wheat flour raw material and cooking it;
   a fermentation step for producing a wheat flour koji by inoculating and cultivating *Aspergillus oryzae* CJ KY (KCCM11302P) on the cooked wheat flour;
   a first aging step by aging a first mixture made by adding a table salt or salt water to the wheat flour koji and mixing the wheat flour koji with at least one ingredient selected from the group consisting of cooked wheat flour, cooked polished rice, cooked soybean, meju and doenjang; and
   a second aging step by adding a dried red pepper flour to the first aged mixture, and by sterilizing and aging a second mixture made by mixing the first mixture obtained from the first aging step with at least one ingredient selected from the group consisting of starch sugar, soy sauce, salt, processed spices, taste and flavor enhancer, cereal product, soy product, meju and doenjang.

2. The method for producing the hot pepper paste according to claim 1, wherein the water content of the cooked wheat flour is 30 to 38 wt. % in the cooking step.

3. The method for producing the hot pepper paste according to claim 1, which comprises making the wheat koji by adding 0.05 to 0.3 wt. % of *Aspergillus oryzae* CJ KY (KCCM11302P), and 0.1 to 1.5 wt. % of an extender, and then by fermenting it at 30 to 40° C. for 3 days, in the fermentation step.

4. The method for producing the hot pepper paste according to claim 1, which comprises
   adding the table salt or salt water to the wheat flour koji at 5 to 10 wt. % in the first aging step,
   mixing the wheat flour koji with 0.1 to 15 wt. % of at least one ingredient selected from the group consisting of cooked wheat flour, cooked soybean, cooked polished rice, meju and doenjang, and
   fermenting it at 25 to 35° C. for 5 to 30 days.

5. The method for producing the hot pepper paste according to claim 1, wherein the first mixture comprises 40 to 55 wt. % of water.

6. The method for producing the hot pepper paste according to claim 1, which comprises:
   in the second aging step,
   sterilizing the second mixture prepared by adding 6 to 25 wt. % of the dried red pepper flour, and 15 to 40 wt. % of at least on ingredient selected from the group consisting of starch sugar, soy sauce, salt, processed spices, taste and flavor enhancer, cereal product, soy product, meju and doenjang to the first aged mixture at 55 to 85° C. for 1 to 60 minutes, and
   adding an edible alcohol to the second mixture and aging it.

\* \* \* \* \*

SEQUENCE LISTING

<160> NUMBER OF SEQ ID NOS: 1

<210> SEQ ID NO 1
<211> LENGTH: 544
<212> TYPE: DNA
<213> ORGANISM: Aspergillus oryzae -continued

```
<400> SEQUENCE: 1
gttctagcga gcccaacctc ccacccgtgt ttactgtacc ttagttgctt cggcgggccc    60
gccattcatg gccgccgggg gctctcagcc ccgggcccgc gcccgccgga gacaccacga    120
actctgtctg atctagtgaa gtctgagttg attgtatcgc aatcagttaa aactttcaac    180
aatggatctc ttggttccgg catcgatgaa gaacgcagcg aaatgcgata actagtgtga    240
attgcagaat tccgtgaatc atcgagtctt tgaacgcaca ttgcgccccc tggtattccg    300
gggggcatgc ctgtccgagc gtcattgctg cccatcaagc acggcttgtg tgttgggtcg    360
tcgtcccctc tccgggggg acgggcccca aaggcagcgg cggcaccgcg tccgatcctc    420
gagcgtatgg ggctttgtca cccgctctgt aggcccggcc ggcgcttgcc gaacgcaaat    480
caatcttttt ccaggttgac ctcggatcag gtagggatac ccgctgaact taagcatatc    540
aaag                                                                544
```